United States Patent [19]

Schoenwald et al.

[11] Patent Number: 4,975,448
[45] Date of Patent: Dec. 4, 1990

[54] 6-AMINO-2-BENZOTHIAZOLESULFONA-MIDE AND TOPICAL TREATMENT COMPOSITIONS AND METHOD FOR GLAUCOMA

[75] Inventors: Ronald D. Schoenwald; Charles F. Barfknecht, both of Iowa City, Iowa

[73] Assignee: University of Iowa Research Foundation, Iowa City, Iowa

[21] Appl. No.: 720,006

[22] Filed: Apr. 4, 1985

Related U.S. Application Data

[63] Continuation-in-part of Ser. No. 464,063, Feb. 13, 1983.

[51] Int. Cl.$^5$ .................. A61K 31/425; C07D 277/62; C07D 277/68; C07D 277/76
[52] U.S. Cl. ..................................... 514/367; 514/913; 548/166
[58] Field of Search ................ 514/367; 548/164, 167, 548/166

[56] References Cited

U.S. PATENT DOCUMENTS 4,499,103  2/1985  de Solmo ........................... 514/365

OTHER PUBLICATIONS

Chem. Abst. 102: 137644(2)(1985) Lewis et al.
Chem. Abst. 102: 197524(c)(1985) Eller et al.

*Primary Examiner*—Douglas W. Robinson
*Attorney, Agent, or Firm*—Zarley, McKee, Thomte, Voorhees & Sease

[57] ABSTRACT

A topical composition for eye treatment of glaucoma, comprising a small but pharmaceutically effective amount of an analog of benzothiazole-2-sulfonamide. The most preferred compound is 6-amino-2-benzothiazolesulfonamide. The invention also relates to a method of topically treating glaucoma with eye drops to reduce intraocular pressure. Finally, disclosed is a method of synthesis of the preferred and highly effective benzothiazole-2-sulfonamide analogs, particularly the 6-amino-2-benzothiazolesulfonamide compound.

14 Claims, No Drawings

6-AMINO-2-BENZOTHIAZOLESULFONAMIDE AND TOPICAL TREATMENT COMPOSITIONS AND METHOD FOR GLAUCOMA

This invention was made in part with government support under Contract No. 5 R01 EY 03297-02 awarded by the National Eye Institute. The government may have certain rights in this invention.

CROSS REFERENCE TO A RELATED INVENTION

This application is a continuation-in-part of copending, commonly assigned application Serial No. 464,063, filed Feb. 13, 1983.

BACKGROUND OF THE INVENTION

Glaucoma, which some estimate affects 2 million adults over 40, is an impairment of vision caused by too much fluid pressure within the eye.

Surgical treatment for glaucoma is effective, however, it is expensive and some surgeons will use surgery only as a last resort.

Carbonic anhydrase inhibitors, prescribed orally work well to treat this disease, but they carry a host of side effects, from nausea to kidney stones.

Glaucoma stems from an excess of fluid behind the cornea, the three-layered tissue that acts as a window to let light enter. Fluid carrying nutrients such as potassium and glucose constantly wash the inside of the cornea to keep it healthy, much as tears wash the outside of the cornea.

In some middle-aged adults fluids build up faster than can be absorbed back into the blood, for one of two reasons: the ciliary body (a tiny tissue behind the iris) may excrete too much fluid, or the fluid may not drain off at the normal rate.

Either way, the excess fluid damages the optic nerve. At first a glaucoma victim usually experiences a subtle loss of peripheral vision—objects will seem to disappear from certain spots to the side. But glaucoma often leads to middle-age blindness.

Unfortunately, the two approaches to general drug usage in treating glaucoma—topical (dropped into the eye) and oral—each have a peculiar set of side effects.

To make the long journey, oral drugs must be dosed in very high concentration. One class of drugs, called carbonic anhydrase inhibitors, slow the formation of fluid by inhibiting a chemical reaction at the ciliary body. Along with their well-tested effectiveness, comes nausea, tingling in fingers and toes and other side effects. Oral drugs generally do not, however, cause side effects in the eye.

Certain topical drugs, while causing less systemic effects, on the other hand, can cause sever headaches and constrict the pupil, making the daytime appear dark.

Accordingly, there is a real and continuing need to develop an inhibitor drug that can be dropped into the eye instead of swallowed, thereby avoiding the present side effects. It is a primary objective of the present invention to develop a highly effective topical carbonic anhydrase inhibitor drug for treatment of glaucoma to reduce intraocular eye pressure, and at the same time, avoid the systemic side effects, commonly caused by oral drugs.

Another objective of the present invention is to develop a drug for topical treatment of glaucoma, which is not only effective, but which will also pass through the three layered cornea and still be effective enough to work on the ciliary body.

Another objective of the present invention is to develop a highly effective, topical drug treatment for glaucoma which is substantially non-harmful to the eye when topically applied.

An even further objective of the present invention is to develop an eye treating topical composition which is effective for glaucoma treatment.

A still further objective is to provide a convenient method of synthesis of 6-amino-2-benzothiazolesulfonamide, which is a highly effective topical treatment of glaucoma.

A further specific objective of the present invention is to provide as a novel component 6-amino-2-benzothiazole-sulfonamide, which in pharmaceutically effective amounts is a highly effective topical composition for eye drop treatment of glaucoma.

The method and manner of achieving each of the above objectives, as well as others, will become apparent from the detailed description of the invention which follows hereinafter.

SUMMARY OF THE INVENTION

As a new compound, 6-amino-2-benzothiazolesulfonamide. Also, topical compositions for eye drop treatment of glaucoma which comprises a small but pharmaceutically effective amount of 6-amino-2-benzothiazolesulfonamide.

The invention thus relates to a most preferred compound which is a compound falling into the general formula presented in our previous patent application, Ser. No. 464,563, filed Feb. 13, 1983. The invention further relates to a method of topically treating glaucoma with eye drops to reduce intraocular eye pressure; and finally, the invention relates to a method of synthesis of this preferred compound.

DETAILED DESCRIPTION OF THE INVENTION

As heretofore mentioned, carbonic anhydrase inhibitors are known. However, the compounds are generally not effective because of the rather severe side effects previously mentioned. Studies have shown that when taken orally, because of the side effects, approximately 80% of the treated patients stop taking the drug treatment within two to three weeks. The side effects that they often report are short-term tingling of the extremities, gastrointestinal tract upset, kidney stones and some renal failure.

The mechanism of reaction of carbonic anhydrase inhibitors has been reported, and it is a combination of a diuretic effect and reduction of intraocular pressure in the eye. The compound useful for treatment in this invention functions to provide reduction of intraocular pressure, but does so without the commonly occurring side effects of oral drugs for treating glaucoma, or the commonly occurring side effects of topical drugs for glaucoma treatment.

The compound developed by the applicant and useful for the topical composition eye drop treatment of glaucoma, as described in this invention, is an analog of benzothiazole-2-sulfonamide, and is a carbonic anhydrase inhibitor. It has the following general formula:

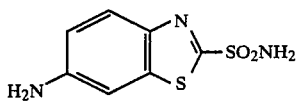

It is also to be understood that one may use an ophthalmologically acceptable salt of the above shown compound. Examples of acceptable salts include the alkali metal salts.

Of course, the compound is carried in an inert, non-eye irritating, non-toxic eye drop diluent of conventional formulation. Such formulations are well known, and commonly referred to in, for example, the *Physician's Desk Reference for Ophthalmology* (1982 Edition, published by Medical Economics Company, Inc., Oridell, N. J.), wherein numerous sterile ophthalmologic ocular solutions are reported, e.g., see pp. 112–114, which are incorporated by reference.

Preferably the amount of 6-amino-2-benzothiazolesulfonamide present in the eye drop treatment composition is a concentration of from about 0.25% to about 5% by weight of the eye drop treating composition. Most preferably, the amount is from about 0.5% to about 3.0% by weight of the eye drop treating composition, and in tests conducted to date, highly effective compositions have used the compounds at the 1% and 3% suspension level.

As heretofore mentioned, while the diluent is not part of the present invention in that such diluents are known, it is preferred that the diluent be an isotonic eye treatment carrier, buffered to a pH within the range of from about 4.0 to about 8.0 and containing a small but effective amount of a wetting agent and an anti-bacterial agent. The preferred pH range is from about 6.8 to about 7.8.

Commonly used wetting agents are well known, and again are mentioned in the previously referred to pages of the *Physician's Desk Reference for Ophthalmology*. One suitable one is Tween, and in particular, Tween 80. Likewise, anti-bacterials are known and commonly employed in such compositions. Suitable anti-bacterials include the most preferred benzalkonium chloride and others as well such as, for example, chlorobutanol. The amount of wetting agent can range from 0.01% to 0.10%.

The amount of anti-bacterial can range from about 0.004% to about 0.02% by weight of the eye drop treating composition.

The compounds of this invention, providing that the molecular structures are as defined hereinbefore, are water soluable, but they also have a lipid solubility factor to allow transfer across the eye, and they have suitable structure to allow them to effectively function in the eye as carbonic anhydrase inhibitors. Their water solubility means ease of preparation for topical application, their lipid solubility characteristics mean effectiveness in transfer across the three corneal layer.

As will be explained hereinafter, the dosage amounts can vary, and no doubt will vary, but are well within routine experimentation of the treating physician. In some of the tests described hereinafter, the dosage for the topical application has been three drops, with one drop every two minutes. This has been found to be effective, but it is also reasonable to expect that other dosage levels will vary depending upon severity of the case.

The following examples are offered to further illustrate the synthesis of the compounds of this invention, the making of topical treatment compositions using the same, and to provide data showing decrease of intraocular pressure in the eyes of rabbits and cynomolgous monkeys. They are intended to further illustrate, but not necessarily limit the invention and it is understood that certain modifications and changes, both in technique and composition and structure, may be made, without departing from structure, function and operation of the invention.

EXAMPLES

EXAMPLE 1

Synthesis of 6-amino-2-benzothiazolesulfonamide

The title compound is prepared by first converting 2-mercaptobenzothiazole to 6-nitro-2-benzothiazolesulfonamide and then reducing to the 6-amino analog. 2-Mercaptobenzothiazole was converted to 2,2'-bis-benzothiazole disulfide in 90% yield: m.p. 175–177° C. Nitration in concentrated sulfuric acid gave 6-nitro-2-mercaptobenzothiazole in 59%. m.p. 255–258° C. The sulfenamide was formed by reaction with aqueous sodium hydroxide and sodium hypochlorite and oxidized in the next step without further purification. The oxidation was accomplished by dissolving the sulfenamide in dimethoxyethane, cooling the solution to $-5°$ C., adding the m-chloroperoxybenzoic acid in dimethoxyethane and working up the reaction in the standard manner to obtain a 70% yield: m.p. 179–180°; MS, m/e 259 (M, calcd. 259). Anal. ($C_7H_5N_3O_4S_2$) CHN.

A mixture of 6-nitrobenzothiazole-2-sulfonamide (3.0 g, 0.011 mol), 95% ethanol (290 ml), and 10% Pd on carbon (3.0 g) was hydrogenated at an initial pressure of 50 psig for 36 hours during which time the theoretical amount of hydrogen was consumed. The reduction mixture was vacuum filtered through a pad of Celite contained in a Buchner funnel and the volatiles removed under reduced pressure. The resulting product was purified by dissolving in aqueous 10% sodium carbonate (25 ml), filtering and adjusting the pH of the filtrate to 6 with glacial acetic acid. The precipitated product was collected by vacuum filtration in a Buchner funnel and dried under reduced pressure at 78° C. in an Abderhalden to give 2.2 g (82.9% yield) of 6-aminobenzothiazole-2-sulfonamide: m.p. 221°–222° C., Anal. ($C_7H_7N_3O_2S_2$) CHN.

EXAMPLE 2

Measurement of Intraocular Pressure ("Salted Rabbit Test") (IOP)

For reasons that are not quite fully understood, it has been found that if the rabbits prior to exsanguanation are treated with a salt diet, the test results are more reproducible and accurate. White rabbits (3–4 months old) were maintained on a diet containing 0.3% sodium chloride for three weeks prior to the start of the experiment.

In particular, a 1% w/v suspension of 6-amino-2-benzothiazolesulfonamide was prepared in a standard vehicle consisting of aqueous pH 7.8 phosphate buffer, 0.05% w/v tween 80, and sufficient NaCl to make the preparation isotonic. One drop, followed by two drops each at one minute intervals, was applied to one eye of normal white rabbits. Twelve rabbits were used in the experiment. The treated eye was selected randomly, whereas, the fellow eye received placebo drops. The observer was masked. The intraocular pressure (IOP) was measured with an Alcon implantation pneumotonometer. A drop of local anesthetic (proparacaine 0.5%) was applied just prior to making the measurement. The IOP was measured in both rabbit eyes through 180 minutes following instillation of the new antiglaucoma agent. The results are shown as follows. Changes in IOP were expressed as:

$$IOP \text{ change} = IOP \text{ (dosed eye} - \text{control eye)}_t -$$
$$IOP \text{ (dosed eye prior to administration} - \text{control eye)}_{t=0}$$

Intraocular Pressure (IOP) Measurements of 6-amino-2-benzothiazolesulfonamide in rabbits[a] maintained on 0.3% sodium chloride drinking water following topical instillation.[b] [b]The dose to the eye was 50 μl of a 1% suspension q 2 minutes for 3 doses

| Time after dosing (minutes) | Ave. change in IOP (mm Hg) | Probability[c] |
|---|---|---|
| 0 | 0 | |
| 20 | −1.7 | <.004 |
| 40 | −2.3 | .0002 |
| 60 | −2.4 | .0003 |
| 80 | −2.5 | .0004 |
| 100 | −1.8 | .004 |
| 120 | −1.8 | .004 |
| 140 | −1.3 | .03 |
| 160 | −1.9 | .004 |
| 180 | −2.5 | .0001 |

[a]N=12 rabbits
[b]The dose to the eye was 50 μl of a 1% suspension q 2 minutes for 3 doses
[c]Probability that the reduction in IOP is due to chance, from student's t test

EXAMPLE 3

As demonstrated in the earlier examples, the compound of the present invention has been demonstrated to inhibit carbonic anhydrase, using the rabbit as the test species. Because there are certain differences in the eyes of rabbits and man, it was desired to test topical carbonic anhydrase inhibition by the compound of the present invention in a subhuman primate species to confirm the presence of activity by this route. The cynomologous monkey was chosen to represent the species. Because drug effects on intraocular pressure are sometimes less dramatic or not demonstrable using an eye that is normotensive, a test protocol known as the "DeSantis" test was developed. It involves testing the carbonic anhydrase inhibitor effects in eyes made hypertensive by laser treatment. In particular, argon laser energy was delivered to the trabecular meshwork of cynomologous monkeys which resulted in an elevation of the intraocular pressure as measured by pneumatonometry. After the eye was allowed to recover from the inflammatory process which accompanied the laser treatment, it was used to test the subject drugs. Experimental results of these tests are reported below.

Intraocular pressure (IOP) was determined using an Alcon Pneumatonograph after light corneal anesthesia with proparacaine, before and at 1, 3 and 7 hours after installation of drug to both eyes of each of six cynomologous monkeys per group. The right eyes of these monkeys had been given laser trabeculoplasty several months prior to this experiment which resulted in ocular hypertension. Animals were trained to sit in restraint chairs and to accept the pressure measurement. Following the measurement, residual anesthetic was washed out with saline.

Data for the intraocular pressure studies are presented in the attached tables, where the lasered eyes but not the normal eyes show significant reduction of intraocular pressure compared to control animals.

In the tables below "OD"refers to ocular dexter, and "OS" refers to ocular sinnister. This is simply another way of saying right and left eye. The designation number in the lefthand column of each table refers to the designation number assigned to each monkey. "SE" refers to standard error. Table 1 shows in the first instance a control treatment of the lasered eye with a gel without the active compound of the invention. In the second instance it shows the treatment of the same eye with the drug, that is with 6-amino-2-benzothiazolesulfonamide. In the third instance it shows a left eye control and in the fourth instance treatment of the left eye with the drug.

TABLE 1

| | | 1.0% 6-Amino-2-benzothiazolesulfonamide Gel | | | | | | |
|---|---|---|---|---|---|---|---|---|
| | | | IOP (mm Hg) | | | | | |
| MONKEY # | EYE | TREATMENT | TIME (HR) | IOP | TIME (HR) | IOP | TIME (HR) | IOP |
| 48 | OD | DRUG | 0 | 60 | 3 | 52 | 6 | 50 |
| 52 | OD | DRUG | 0 | 58 | 3 | 37 | 6 | 46 |
| 55 | OD | DRUG | 0 | 25 | 3 | 27 | 6 | 30 |
| 56 | OD | DRUG | 0 | 47 | 3 | 35 | 6 | 37 |
| 63 | OD | DRUG | 0 | 55 | 3 | 33 | 6 | 25 |
| 187 | OD | DRUG | 0 | 39 | 3 | 25 | 6 | 31 |
| MEAN | | | | 47.3 | | 34.8 | | 36.5 |
| S.E. | | | | 5.5 | | 3.9 | | 4.0 |
| MEAN | % CHANGE | | | | | −23.8 | | −19.0 |
| S.E. | | | | | | 7.5 | | 9.7 |
| 49 | OD | CONTROL | 0 | 34 | 3 | 27 | 6 | 30 |
| 53 | OD | CONTROL | 0 | 60 | 3 | 48 | 6 | 40 |
| 60 | OD | CONTROL | 0 | 30 | 3 | 30 | 6 | 30 |
| 62 | OD | CONTROL | 0 | 62 | 3 | 53 | 6 | 54 |
| 64 | OD | CONTROL | 0 | 48 | 3 | 35 | 6 | 33 |
| 186 | OD | CONTROL | 0 | 30 | 3 | 32 | 6 | 32 |
| MEAN | | | | 44.0 | | 37.5 | | 36.5 |
| S.E. | | | | 6.0 | | 4.3 | | 3.8 |
| MEAN | % CHANGE | | | | | −12.6 | | −13.8 |
| S.E. | | | | | | 5.4 | | 6.6 |
| 48 | OS | DRUG | 0 | 22 | 3 | 23 | 6 | 21 |
| 52 | OS | DRUG | 0 | 25 | 3 | 23 | 6 | 26 |
| 55 | OS | DRUG | 0 | 25 | 3 | 26 | 6 | 25 |

TABLE 1-continued

1.0% 6-Amino-2-benzothiazolesulfonamide Gel

| MONKEY # | EYE | TREATMENT | TIME (HR) | IOP | TIME (HR) | IOP | TIME (HR) | IOP |
|---|---|---|---|---|---|---|---|---|
| 56 | OS | DRUG | 0 | 33 | 3 | 30 | 6 | 33 |
| 63 | OS | DRUG | 0 | 23 | 3 | 22 | 6 | 22 |
| 187 | OS | DRUG | 0 | 35 | 3 | 35 | 6 | 35 |
| MEAN | | | | 27.2 | | 26.5 | | 27.0 |
| S.E. | | | | 2.2 | | 2.1 | | 2.4 |
| MEAN | % CHANGE | | | | | −2.2 | | −0.8 |
| S.E. | | | | | | 2.4 | | 1.3 |
| 49 | OS | CONTROL | 0 | 30 | 3 | 24 | 6 | 30 |
| 53 | OS | CONTROL | 0 | 28 | 3 | 24 | 6 | 25 |
| 60 | OS | CONTROL | 0 | 25 | 3 | 28 | 6 | 30 |
| 62 | OS | CONTROL | 0 | 25 | 3 | 25 | 6 | 22 |
| 64 | OS | CONTROL | 0 | 32 | 3 | 30 | 6 | 34 |
| 186 | OS | CONTROL | 0 | 29 | 3 | 25 | 6 | 27 |
| MEAN | | | | 28.2 | | 26.0 | | 28.0 |
| S.E. | | | | 1.1 | | 1.0 | | 1.7 |
| MEAN | % CHANGE | | | | | −7.1 | | −0.6 |
| S.E. | | | | | | 4.8 | | 5.0 |

**NOTE:
Percent change values are calculated from individual animal data and may not reflect changes of mean IOP.

A repeat in order to test the accuracy of the data for the same monkeys was conducted six days later and is reported in Table 2.

TABLE 2

1.0% 6-Amino-2-benzothiazolesulfonamide Gel (Six Days Later)

| MONKEY # | EYE | TREATMENT # | TIME (HR) | IOP | TIME (HR) | IOP | TIME (HR) | IOP | TIME (HR) | IOP |
|---|---|---|---|---|---|---|---|---|---|---|
| 59 | OD | DRUG | 0 | 55 | 1 | 57 | 3 | 50 | 7 | 44 |
| 51 | OD | DRUG | 0 | 60 | 1 | 49 | 3 | 43 | 7 | 51 |
| 48 | OD | DRUG | 0 | 57 | 1 | 62 | 3 | 55 | 7 | 45 |
| 180 | OD | DRUG | 0 | 44 | 1 | 44 | 3 | 40 | 7 | 42 |
| 211 | OD | DRUG | 0 | 61 | 1 | 61 | 3 | 56 | 7 | 62 |
| 203 | OD | DRUG | 0 | 47 | 1 | 47 | 3 | 40 | 7 | 56 |
| MEAN | | | | 54.0 | | 53.3 | | 47.3 | | 50.0 |
| S.E. | | | | 2.9 | | 3.1 | | 3.0 | | 3.2 |
| MEAN | % CHANGE | | | | | −1.0 | | −12.2 | | −6.7 |
| S.E. | | | | | | 3.7 | | 3.5 | | 6.3 |
| 59 | OS | DRUG | 0 | 22 | 1 | 27 | 3 | 25 | 7 | 28 |
| 51 | OS | DRUG | 0 | 25 | 1 | 24 | 3 | 25 | 7 | 26 |
| 48 | OS | DRUG | 0 | 21 | 1 | 21 | 3 | 21 | 7 | 21 |
| 180 | OS | DRUG | 0 | 25 | 1 | 27 | 3 | 26 | 7 | 27 |
| 211 | OS | DRUG | 0 | 24 | 1 | 21 | 3 | 19 | 7 | 19 |
| 203 | OS | DRUG | 0 | 16 | 1 | 19 | 3 | 19 | 7 | 19 |
| MEAN | | | | 22.2 | | 23.2 | | 22.5 | | 23.3 |
| S.E. | | | | 1.4 | | 1.4 | | 1.3 | | 1.7 |
| MEAN | % CHANGE | | | | | +5.5 | | +2.6 | | +6.2 |
| S.E. | | | | | | 5.5 | | 5.6 | | 6.8 |
| 181 | OD | CONTROL | 0 | 70 | 1 | 55 | 3 | 55 | 7 | 57 |
| 210 | OD | CONTROL | 0 | 63 | 1 | 67 | 3 | 63 | 7 | 61 |
| 199 | OD | CONTROL | 0 | 57 | 1 | 58 | 3 | 56 | 7 | 56 |
| 61 | OD | CONTROL | 0 | 65 | 1 | 71 | 3 | 68 | 7 | 71 |
| 58 | OD | CONTROL | 0 | 66 | 1 | 66 | 3 | 51 | 7 | 43 |
| 213 | OD | CONTROL | 0 | 70 | 1 | 75 | 3 | 73 | 7 | 72 |
| MEAN | | | | 65.2 | | 65.3 | | 61.0 | | 60.0 |
| S.E. | | | | 2.0 | | 3.1 | | 3.5 | | 4.4 |
| MEAN | % CHANGE | | | | | +0.5 | | −6.2 | | −7.7 |
| S.E. | | | | | | 4.6 | | 5.1 | | 6.6 |
| 181 | OS | CONTROL | 0 | 22 | 1 | 25 | 3 | 24 | 7 | 25 |
| 210 | OS | CONTROL | 0 | 23 | 1 | 24 | 3 | 25 | 7 | 23 |
| 199 | OS | CONTROL | 0 | 19 | 1 | 19 | 3 | 19 | 7 | 20 |
| 61 | OS | CONTROL | 0 | 16 | 1 | 17 | 3 | 18 | 7 | 18 |
| 58 | OS | CONTROL | 0 | 25 | 1 | 26 | 3 | 23 | 7 | 23 |
| 213 | OS | CONTROL | 0 | 28 | 1 | 29 | 3 | 29 | 7 | 28 |
| MEAN | | | | 22.2 | | 23.3 | | 23.0 | | 22.8 |
| S.E. | | | | 1.7 | | 1.8 | | 1.7 | | 1.4 |
| MEAN | % CHANGE | | | | | +5.3 | | +4.3 | | +3.9 |
| S.E. | | | | | | 1.9 | | 3.1 | | 3.4 |

**NOTE:
Percent change values are calculated from individual animal data and may not reflect changes of mean IOP.

TABLE 3

3.0% 6-Amino-2-benzothiazolesulfonamide Gel

| MONKEY # | EYE | TREATMENT | INTRACULAR PRESSURE (mm Hg) at HOUR # FOLLOWING DOSAGE | | | | | |
|---|---|---|---|---|---|---|---|---|
| | | | 0 | 1 | 3 | 7 | 26 | 29 |
| 190 | OD | DRUG | 57 | 54 | 50 | 43 | 52 | 57 |
| 202 | OD | DRUG | 52 | 40 | 35 | 33 | 38 | 35 |
| 188 | OD | DRUG | 34 | 28 | 25 | 28 | 30 | 30 |
| 177 | OD | DRUG | 54 | 53 | 42 | 41 | 52 | 56 |
| 205 | OD | DRUG | 54 | 41 | 35 | 31 | 45 | 48 |
| 195 | OD | DRUG | 43 | 23 | 25 | 27 | 23 | 38 |
| MEAN | | | 49.0 | 39.8 | 35.3 | 33.8 | 40.0 | 44.0 |
| S.E. | | | 3.6 | 5.2 | 4.0 | 2.7 | 4.9 | 4.6 |
| MEAN | % CHANGE | | | −19.8 | −28.5 | −30.5 | −19.1 | −10.6 |
| S.E. | | | | 6.5 | 4.3 | 3.9 | 6.4 | .5.2 |
| 190 | OS | DRUG | 28 | 28 | 28 | 28 | 29 | 29 |
| 202 | OS | DRUG | 23 | 24 | 21 | 23 | 24 | 24 |
| 188 | OS | DRUG | 22 | 26 | 22 | 25 | 24 | 24 |
| 177 | OS | DRUG | 21 | 19 | 19 | 21 | 18 | 19 |
| 205 | OS | DRUG | 28 | 27 | 24 | 27 | 28 | 27 |
| 195 | OS | DRUG | 28 | 28 | 25 | 27 | 27 | 24 |
| MEAN | | | 25.0 | 25.3 | 23.2 | 25.2 | 25.0 | 24.5 |
| S.E. | | | 1.4 | 1.4 | 1.3 | 1.1 | 1.6 | 1.4 |
| MEAN | % CHANGE | | | +1.6 | −7.2 | +1.1 | −0.1 | −1.7 |
| S.E. | | | | 3.8 | 2.4 | 2.6 | 3.3 | 3.7 |
| 182 | OD | CONTROL | 64 | 62 | 58 | 61 | 64 | 63 |
| 208 | OD | CONTROL | 56 | 57 | 48 | 52 | 52 | 49 |
| 200 | OD | CONTROL | 37 | 27 | 25 | 37 | 23 | 23 |
| 207 | OD | CONTROL | 61 | 59 | 57 | 61 | 55 | 51 |
| 209 | OD | CONTROL | 62 | 62 | 58 | 54 | 60 | 60 |
| 201 | OD | CONTROL | 37 | 28 | 28 | 30 | 24 | 18 |
| MEAN | | | 52.8 | 49.2 | 45.7 | 49.2 | 46.3 | 44.0 |
| S.E. | | | 5.1 | 6.9 | 6.3 | 5.2 | 7.4 | 7.8 |
| MEAN | % CHANGE | | | −9.3 | −15.6 | −7.3 | −15.5 | −20.5 |
| S.E. | | | | 5.2 | 4.3 | 3.1 | 6.8 | 8.1 |
| 182 | OS | CONTROL | 24 | 22 | 24 | 25 | 24 | 22 |
| 208 | OS | CONTROL | 24 | 24 | 24 | 24 | 24 | 25 |
| 200 | OS | CONTROL | 23 | 22 | 21 | 24 | 23 | 23 |
| 207 | OS | CONTROL | 25 | 27 | 28 | 28 | 27 | 25 |
| 209 | OS | CONTROL | 25 | 28 | 23 | 24 | 24 | 26 |
| 201 | OS | CONTROL | 27 | 24 | 22 | 24 | 23 | 24 |
| MEAN | | | 24.7 | 24.5 | 23.7 | 24.8 | 24.2 | 24.2 |
| S.E. | | | 0.6 | 1.0 | 1.0 | 0.7 | 0.6 | 0.6 |
| MEAN | % CHANGE | | | −0.6 | −3.9 | +0.9 | −1.8 | −1.9 |
| S.E. | | | | 3.7 | 4.2 | 3.2 | 3.1 | 2.6 |

**NOTE:
Percent change values are calculated from individual animal data and may not reflect changes of mean IOP.

TABLE 4

3.0% 6-Amino-2-benzothiazolesulfonamide Gel

| MONKEY # | EYE | TREATMENT | IOP (mm Hg) | | | | | | | |
|---|---|---|---|---|---|---|---|---|---|---|
| | | | TIME (HR) | IOP | TIME (HR) | IOP | TIME (HR) | IOP | TIME (HR) | IOP |
| 59 | OD | DRUG | 0 | 55 | 1 | 58 | 3 | 45 | 7 | 32 |
| 53 | OD | DRUG | 0 | 54 | 1 | 52 | 3 | 50 | 7 | 60 |
| 210 | OD | DRUG | 0 | 58 | 1 | 56 | 3 | 52 | 7 | 47 |
| 181 | OD | DRUG | 0 | 54 | 1 | 53 | 3 | 47 | 7 | 50 |
| 213 | OD | DRUG | 0 | 73 | 1 | 73 | 3 | 65 | 7 | 65 |
| 48 | OD | DRUG | 0 | 52 | 1 | 52 | 3 | 45 | 7 | 37 |
| MEAN | | | | 57.7 | | 57.3 | | 50.7 | | 48.5 |
| S.E. | | | | 3.2 | | 3.3 | | 3.1 | | 5.2 |
| MEAN | % CHANGE | | | | | −0.6 | | −12.0 | | −16.2 |
| S.E. | | | | | | 1.4 | | 1.5 | | 7.5 |
| 59 | OS | DRUG | 0 | 32 | 1 | 31 | 3 | 32 | 7 | 30 |
| 53 | OS | DRUG | 0 | 30 | 1 | 26 | 3 | 24 | 7 | 26 |
| 210 | OS | DRUG | 0 | 24 | 1 | 25 | 3 | 25 | 7 | 27 |
| 181 | OS | DRUG | 0 | 28 | 1 | 30 | 3 | 25 | 7 | 27 |
| 213 | OS | DRUG | 0 | 34 | 1 | 25 | 3 | 25 | 7 | 30 |
| 48 | OS | DRUG | 0 | 22 | 1 | 20 | 3 | 21 | 7 | 22 |
| MEAN | | | | 28.3 | | 26.2 | | 25.3 | | 27.0 |
| S.E. | | | | 1.9 | | 1.6 | | 1.5 | | 1.2 |
| MEAN | % CHANGE | | | | | −6.8 | | −9.6 | | −3.8 |
| S.E. | | | | | | 5.4 | | 4.8 | | 3.8 |
| 211 | OD | CONTROL | 0 | 53 | 1 | 51 | 3 | 57 | 7 | 55 |
| 51 | OD | CONTROL | 0 | 51 | 1 | 57 | 3 | 50 | 7 | 50 |
| 206 | OD | CONTROL | 0 | 56 | 1 | 54 | 3 | 53 | 7 | 53 |
| 64 | OD | CONTROL | 0 | 40 | 1 | 40 | 3 | 38 | 7 | 30 |
| 203 | OD | CONTROL | 0 | 58 | 1 | 49 | 3 | 47 | 7 | 47 |
| 199 | OD | CONTROL | 0 | 53 | 1 | 54 | 3 | 53 | 7 | 55 |
| MEAN | | | | 51.8 | | 50.8 | | 49.7 | | 48.3 |

TABLE 4-continued

| | | | \multicolumn{8}{c}{3.0% 6-Amino-2-benzothiazolesulfonamide Gel} |
|---|---|---|---|---|---|---|---|---|---|---|

| MONKEY # | EYE | TREATMENT | TIME (HR) | IOP | TIME (HR) | IOP | TIME (HR) | IOP | TIME (HR) | IOP |
|---|---|---|---|---|---|---|---|---|---|---|
| S.E. | | | | 2.6 | | 2.4 | | 2.7 | | 3.9 |
| MEAN | % CHANGE | | | | | −1.5 | −4.0 | | −7.3 | |
| S.E. | | | | | | 3.6 | | 3.6 | | 4.9 |
| 211 | OS | CONTROL | 0 | 27 | 1 | 26 | 3 | 25 | 7 | 17 |
| 51 | OS | CONTROL | 0 | 29 | 1 | 31 | 3 | 26 | 7 | 30 |
| 206 | OS | CONTROL | 0 | 26 | 1 | 24 | 3 | 27 | 7 | 27 |
| 64 | OS | CONTROL | 0 | 36 | 1 | 35 | 3 | 33 | 7 | 25 |
| 203 | OS | CONTROL | 0 | 28 | 1 | 20 | 3 | 22 | 7 | 25 |
| 199 | OS | CONTROL | 0 | 23 | 1 | 22 | 3 | 25 | 7 | 25 |
| MEAN | | | | 28.2 | | 26.3 | | 26.3 | | 26.5 |
| S.E. | | | | 1.8 | | 2.3 | | 1.5 | | 2.4 |
| MEAN | % CHANGE | | | | | −6.7 | | −5.8 | | −5.7 |
| S.E. | | | | | | 4.8 | | 4.4 | | 6.8 |

**NOTE:
Percent change values are calculated from individual animal data and may not reflect changes of mean IOP.

From an examination of the data presented in this example, as well as Tables 1-3, it can be seen that 6-amino-2-benzothiazolesulfonamide is an effective treating composition for topical treatment of glaucoma in mammalian species such as rabbits and in subhuman primates such as cynomologous monkeys.

What is claimed is:

1. 6-Amino-2-benzothiazolesulfonamide

2. A topical composition for eye drop treatment of glaucoma comprising a small but intraocular pressure lowering effective amount of 6-amino-2-benzothiazolesulfonamide, carbonic anhydrase inhibitor of the formula:

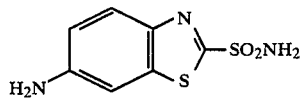

or an opthalmologically acceptable salt thereof; and an inert, non-eye irritating, non-toxic eye drop diluent.

3. The composition of claim 2 wherein said sulfonamide is at a concentration of from about b 0.25% to about 5% by weight of said eye drop treating composition.

4. The composition of claim 2 wherein said sulfonamide is about 0.5% to about 3.0% by weight of said eye drop treating composition.

5. The composition of claim 3 wherein said sulfonamide is about 1% by weight of said eye drop treating composition.

6. The composition of claim 1 wherein said diluent is an isotonic eye treatment carrier, diluent formulation buffered to a pH of from about 4.0 to about 8.0, and containing small but effective amounts of a wetting agent and an anti-bacterial agent.

7. The composition of claim 2 wherein said diluent is an isotonic eye treatment carrier, diluent formulation buffered to a pH of from about 6.8 to about 7.8, and containing small but effective amounts of a wetting agent and an anti-bacterial agent.

8. The composition of claim 5 wherein said wetting agent is a wetting agent of pharmaceutical acceptability.

9. The composition of claim 7 wherein said wetting agent is Tween 80.

10. The composition of claim 6 wherein said anti-bacterial agent is benzalkonium chloride.

11. The composition of claim 9 wherein the amount of said anti-bacterial is from 0.004% to 0.02% by weight of said eye drop treatment composition.

12. The composition of claim 2 wherein said diluent is a gel.

13. A method of topically treating glaucoma with eye drops to reduce intraocular eye pressure, said method comprising: topically applying to the eye a small, but intraocular pressure lowering effective amount of 6-amino-2-benzothiazolesulfonamide or an ophthalmologically acceptable salt thereof, in combination with an inert, non-irritating non-toxic eye drop diluent.

14. The method of claim 13 wherein said 6-amino-2-benzothiazolesulfonamide is present at a concentration of from about 0.25% to about 5.0% by weight of said compound and diluent combination.

* * * * *